US009182210B2

(12) United States Patent
Brookover et al.

(10) Patent No.: US 9,182,210 B2
(45) Date of Patent: Nov. 10, 2015

(54) CALIPER FOR MEASUREMENT OF AN OBJECT

(71) Applicant: OSSUR HF, Reykjavik (IS)

(72) Inventors: Derek Brookover, Irvine, CA (US); Jason Robert Taylor, Aliso Viejo, CA (US)

(73) Assignee: OSSUR HF, Reykjavik (IS)

( * ) Notice: Subject to any disclaimer, the term of this patent is extended or adjusted under 35 U.S.C. 154(b) by 128 days.

(21) Appl. No.: 14/011,129

(22) Filed: Aug. 27, 2013

(65) Prior Publication Data

US 2014/0059873 A1 Mar. 6, 2014

Related U.S. Application Data

(60) Provisional application No. 61/694,474, filed on Aug. 29, 2012.

(51) Int. Cl.
*G01B 3/20* (2006.01)
*A61B 5/00* (2006.01)
*A61B 5/107* (2006.01)

(52) U.S. Cl.
CPC ............... *G01B 3/20* (2013.01); *A61B 5/1072* (2013.01); *A61B 5/6828* (2013.01)

(58) Field of Classification Search
CPC ........................................................ G01B 3/20
USPC ................................................... 33/512, 783
See application file for complete search history.

(56) References Cited

U.S. PATENT DOCUMENTS

| 399,167 | A | * | 3/1889 | Starrett | 33/796 |
|---|---|---|---|---|---|
| 1,007,229 | A | * | 10/1911 | Nielsen | 33/810 |
| 1,294,723 | A | * | 2/1919 | Swinburne | 33/811 |
| 1,621,526 | A | * | 3/1927 | Culell | 33/796 |
| 2,318,864 | A | | 5/1943 | Jackson | |
| 2,980,110 | A | | 4/1961 | Brumfield et al. | |
| 3,008,239 | A | | 11/1961 | Lange | |
| 3,140,546 | A | | 7/1964 | Bartlett | |
| 3,953,900 | A | | 5/1976 | Thompson | |
| 4,008,523 | A | * | 2/1977 | von Voros | 33/784 |
| 4,315,372 | A | | 2/1982 | Kinkead | |
| 4,776,327 | A | | 10/1988 | Russell | |
| 4,807,605 | A | | 2/1989 | Mattingly | |
| 4,827,916 | A | | 5/1989 | Kosova | |
| 4,843,720 | A | * | 7/1989 | Kim | 33/812 |
| 5,038,795 | A | * | 8/1991 | Roush et al. | 600/587 |
| 5,443,510 | A | | 8/1995 | Shetty et al. | |
| 5,556,373 | A | | 9/1996 | Motloch | |
| 5,662,594 | A | | 9/1997 | Rosenblatt | |

(Continued)

OTHER PUBLICATIONS

"Digital Measuring System for Unloader & CTi CM Braces", OSSUR, Aug. 1, 2012.

(Continued)

*Primary Examiner* — Christopher Fulton
(74) *Attorney, Agent, or Firm* — Workman Nydegger

(57) ABSTRACT

A caliper is arranged for applying predetermined constant pressure to a joint or other anatomy under measurement. The caliper includes an elongate housing, a first jaw connected to the housing, a second jaw slidably connected to the housing, the first and second jaws spaced apart by a predetermined minimum distance, and a constant force spring engaging the first and second jaws. The constant force spring biases the first and second jaws toward one another. A method includes using the caliper to measure anatomical dimensions.

17 Claims, 5 Drawing Sheets

(56) References Cited

U.S. PATENT DOCUMENTS

| | | |
|---|---|---|
| 5,741,215 A | 4/1998 | D'Urso |
| 5,768,134 A | 6/1998 | Swaelens et al. |
| 5,857,987 A | 1/1999 | Habermeyer |
| 5,880,964 A | 3/1999 | Schall et al. |
| 5,888,216 A | 3/1999 | Haberman |
| 6,236,743 B1 | 5/2001 | Pratt |
| 6,427,695 B1 | 8/2002 | Zanetti et al. |
| 6,540,708 B1 | 4/2003 | Manspeizer |
| 6,553,685 B2 * | 4/2003 | Nishina et al. ............... 33/815 |
| 6,564,086 B2 | 5/2003 | Marchitto et al. |
| 6,572,571 B2 | 6/2003 | Lowe |
| 6,597,965 B2 | 7/2003 | Graves et al. |
| 6,613,006 B1 | 9/2003 | Asherman |
| 6,725,118 B1 | 4/2004 | Fried et al. |
| 6,726,641 B2 | 4/2004 | Chiang et al. |
| 6,968,246 B2 | 11/2005 | Watson et al. |
| 7,127,101 B2 | 10/2006 | Littlefield et al. |
| 7,210,926 B2 | 5/2007 | Tadros et al. |
| 7,242,798 B2 | 7/2007 | Littlefield et al. |
| 7,340,316 B2 | 3/2008 | Spaeth et al. |
| 7,661,170 B2 | 2/2010 | Goode et al. |
| 7,735,237 B1 * | 6/2010 | Moon ............... 33/783 |
| 7,797,072 B2 | 9/2010 | Summit |
| 7,896,827 B2 | 3/2011 | Ingimundarson et al. |
| 8,005,651 B2 | 8/2011 | Summit et al. |
| 8,059,917 B2 | 11/2011 | Dumas et al. |
| 8,613,716 B2 | 12/2013 | Summit et al. |
| 8,739,428 B2 * | 6/2014 | Emtman ............... 33/815 |
| 2001/0002232 A1 | 5/2001 | Young et al. |
| 2002/0016631 A1 | 2/2002 | Marchitto et al. |
| 2003/0032906 A1 | 2/2003 | Narula et al. |
| 2003/0065259 A1 | 4/2003 | Gateno et al. |
| 2004/0019266 A1 | 1/2004 | Marciante et al. |
| 2004/0068337 A1 | 4/2004 | Watson et al. |
| 2004/0133431 A1 | 7/2004 | Udiljak et al. |
| 2004/0162511 A1 | 8/2004 | Barberio |
| 2004/0230149 A1 | 11/2004 | Littlefield et al. |
| 2004/0236424 A1 | 11/2004 | Berez et al. |
| 2004/0260402 A1 | 12/2004 | Baldini et al. |
| 2005/0004472 A1 | 1/2005 | Pratt |
| 2005/0015172 A1 | 1/2005 | Fried et al. |
| 2005/0043835 A1 | 2/2005 | Christensen |
| 2005/0044740 A1 * | 3/2005 | Hansen ............... 33/783 |
| 2005/0061332 A1 | 3/2005 | Greenawalt et al. |
| 2005/0065458 A1 | 3/2005 | Kim |
| 2006/0100832 A1 | 5/2006 | Bowman |
| 2006/0161267 A1 | 7/2006 | Clausen |
| 2007/0016323 A1 | 1/2007 | Fried |
| 2007/0133850 A1 | 6/2007 | Paez |
| 2007/0225630 A1 | 9/2007 | Wyatt et al. |
| 2008/0120756 A1 | 5/2008 | Shepherd |
| 2008/0294083 A1 | 11/2008 | Chang et al. |
| 2008/0319362 A1 | 12/2008 | Joseph |
| 2009/0088674 A1 | 4/2009 | Caillouette et al. |
| 2009/0254015 A1 | 10/2009 | Segal et al. |
| 2010/0008588 A1 | 1/2010 | Feldkhun et al. |
| 2010/0137770 A1 | 6/2010 | Ingimundarson et al. |
| 2010/0138193 A1 | 6/2010 | Summit et al. |
| 2010/0228646 A1 | 9/2010 | Heidel |
| 2010/0268138 A1 | 10/2010 | Summit et al. |
| 2011/0001983 A1 | 1/2011 | Becker et al. |
| 2011/0056004 A1 | 3/2011 | Landi |
| 2011/0166435 A1 | 7/2011 | Lye |
| 2013/0123668 A1 * | 5/2013 | Rodrigues Quintas et al. ............... 600/595 |

OTHER PUBLICATIONS

International Search Report and Written Opinion from International Application No. PCT/US13/56896, mailed Apr. 23, 2014.

* cited by examiner

CALIPER FOR MEASUREMENT OF AN OBJECT

FIELD OF THE INVENTION

The disclosure relates to an improved device for measuring an object, and more particularly to a caliper having jaws that apply a predetermined constant pressure to a joint or other anatomy under measurement.

BACKGROUND

Various types of calipers are known for measuring different objects. A caliper must be properly applied against the object to take the desired measurement, and when measuring the thickness of between two sides of an object, a caliper must be held at right angles to the piece.

In the field of orthopedics, calipers are used for measuring a knee and a leg for a knee brace. As illustrated in FIG. 1, an exemplary method for measuring a knee includes using a marker to apply landmarks on the patient's leg such as at the medial joint space, and along the tibial crest at the tibial tuberosity and a distance below which is depicted in FIGS. 1A and 1B. Referring to FIG. 1C, a conventional caliper 102 comes into use in the method by taking the M-L (medial-lateral) measurement 109 at the joint space against the patient's condyles. The caliper 102 includes jaws 104, 106 snugly adjusted against the patient's skin to obtain the measurement and are left in place as the measurement is recorded along the scale 108.

In using the mid patella as a reference point, as depicted in FIG. 1D, above and below circumference measurements 105, 107 are taken at specified distances, and a caliper may also obtain M-L measurements at these locations as well. Next, with the patient standing in a weight bearing position facing a camera, the height of the camera is adjusted at a mid-patella level, and the camera is positioned so it is approximately a specified distance away from the patient. The image captures the leg a specified distance above and below mid patella and is taken of the anterior side of the knee, and an additional image is taken of the lateral side of the knee, as shown in FIGS. 1E and 1F.

The conventional caliper may obtain the M-L measurement and other devices have jaws that slide relative to one another and are indexed to a scale located along a shaft. The clinician must adjust one of the jaws relative to the other jaw, manually move the jaw to press against the patient's soft tissue, and manually removes the jaws from the soft tissue upon completion of the measurement. The force against the soft tissue may exceed comfort levels or may be inconsistently applied from patient to patient.

The conventional caliper 102 may have narrow jaws 104, 106 which may shift over the soft tissue due to their narrow width and may cause discomfort because of sharp tips of the jaws. The jaws are typically elongated and straight, and provide little or any space between areas of the soft tissue within the jaws for adjustment by a clinician. A patient's condyles may have an irregular shape and the narrow jaws may fail to provide an accurate measurement of M/L due to condyle irregularity. In variations, conventional calipers may use contoured "cup-shaped" contact point which extend over the condyles but limit the clinician for placement over the condyles.

Due to a variety of leg shapes, sizes and soft tissue amount, conventional calipers provide inconsistent compression over patients' soft tissue due in part to human error by clinician. The inconsistent compression results in improper measurements for the eventual knee brace and may lead to inferior customization of the knee brace.

SUMMARY

Under the embodiments of the invention, a caliper is provided consistent compression over a spectrum of knee phenotypes and soft tissue amounts for uniform measurements across a variety knees. The caliper is not limited to measuring knees and legs, but may be used for other portions of the patient's anatomy and for other applications in measuring an object.

The caliper has a constant force spring that creates consistent, predetermined force throughout its extension and retraction. This provides consistent measurements of the M-L measurement for patients with little soft tissue and with patients with a large amount of soft tissue. This enables more accurate brace sizing across all phenotypes.

The caliper has a flat condyle contact to allow the clinician to align flat portions of the condyle with jaws of the calipers as seen fit according to the patient's knee and size.

The caliper has an effective ergonomic profile that allows the calipers to be easier to grasp and adjust, thereby being useable by clinician with uniformity and minimal complexity.

The numerous other advantages, features and functions of embodiments of the caliper are readily apparent and better understood in view of the following description and accompanying drawings. The following description is not intended to limit the scope of the caliper, but instead merely provides exemplary embodiments for ease of understanding.

BRIEF DESCRIPTION OF THE DRAWINGS

These and other features, aspects, and advantages of the present invention will become better understood regarding the following description, appended claims, and accompanying drawings.

Figure 1:
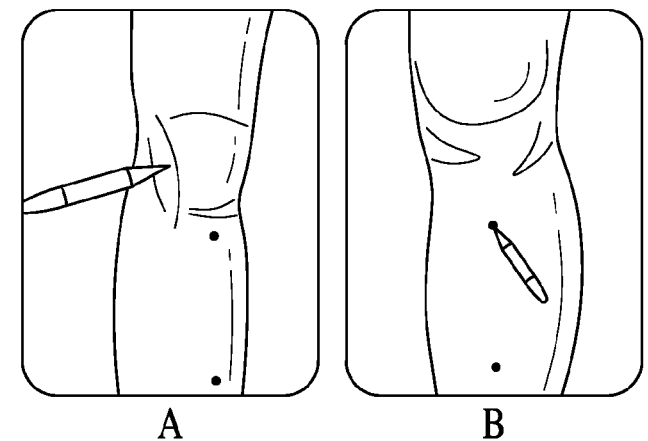
FIG. 1 shows a prior art method and caliper for measuring a knee.
Figure 1:
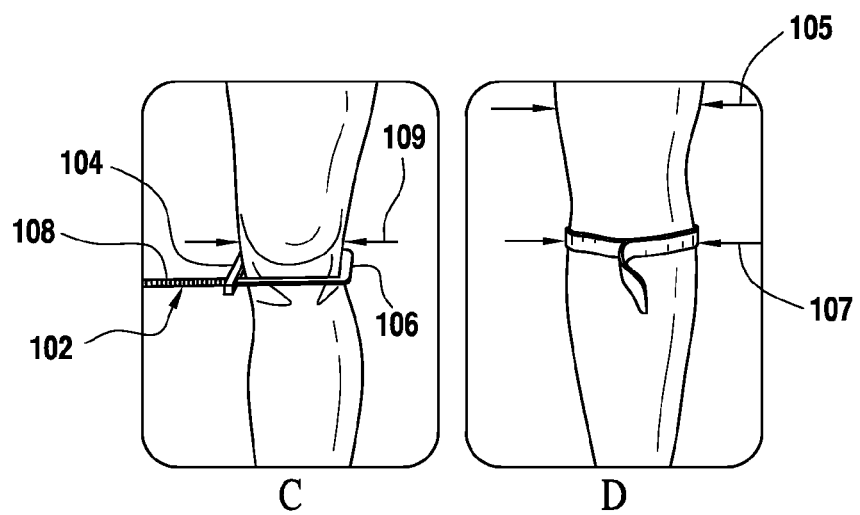
Figure 1:
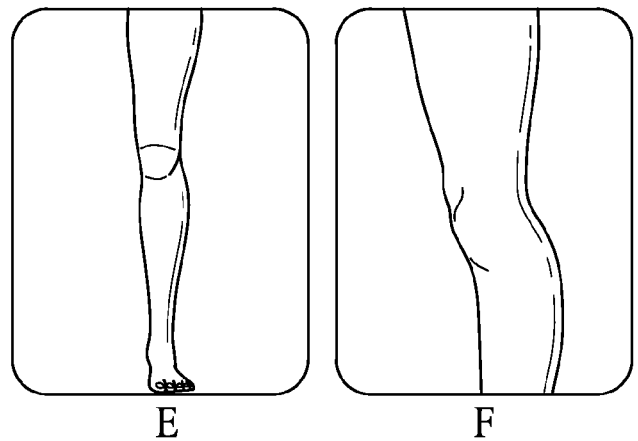
Figure 2:
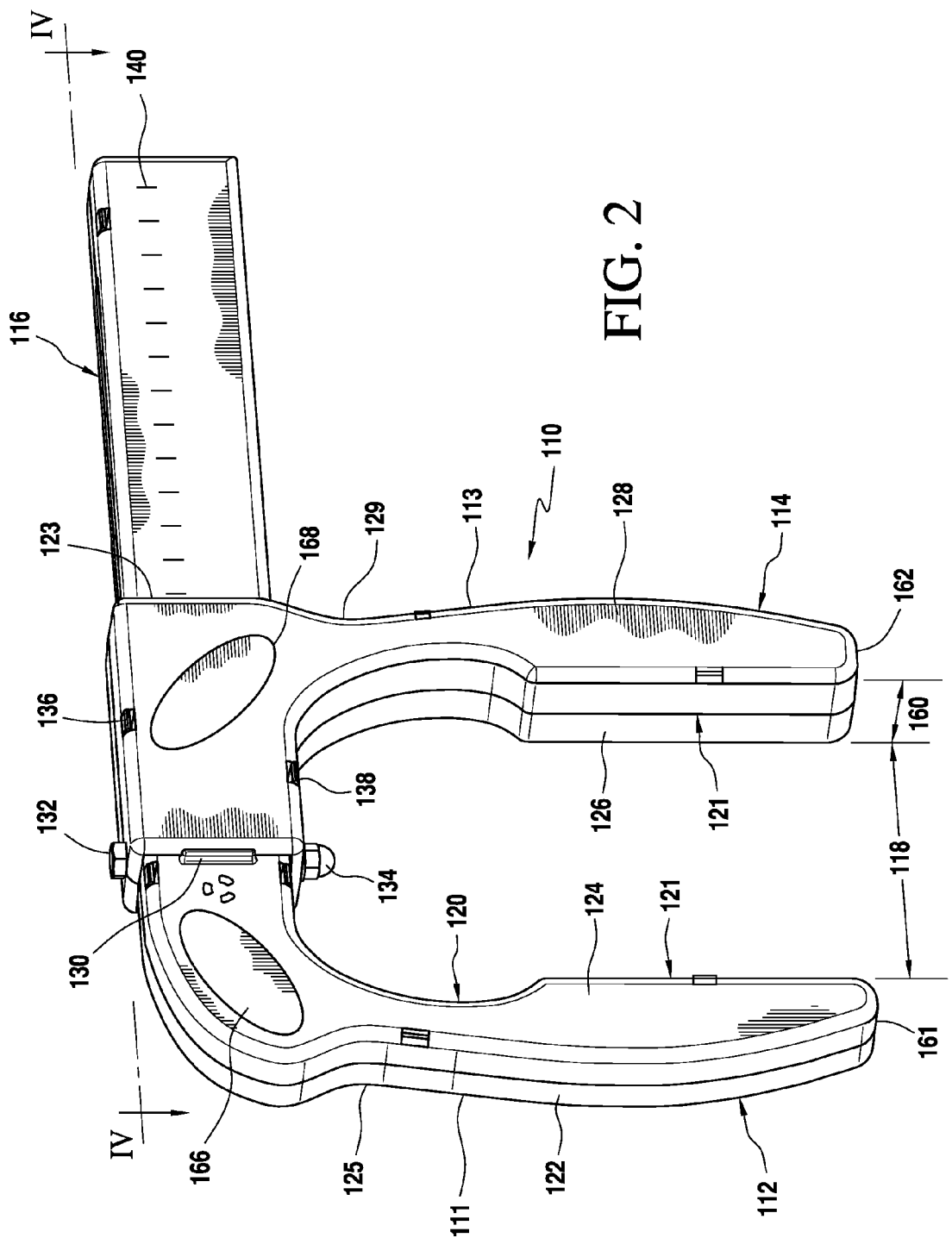
FIG. 2 is a perspective view of an embodiment of a caliper.

The drawing figures are not necessarily drawn to scale, but instead are drawn to provide a better understanding of the components, and are not intended to be limiting in scope, but rather to provide exemplary illustrations. The figures illustrate exemplary embodiments of a prosthetic knee and the components, and in no way limit the structures or configurations of a prosthetic knee and components according to the present disclosure.

DETAILED DESCRIPTION OF VARIOUS EMBODIMENTS

A. Overview

A better understanding of different embodiments of the invention may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

B. Embodiments of the Caliper

According to the embodiment of FIGS. 2-5, an exemplary caliper 110 is arranged for measuring a leg and knee joint, particularly the distance between the medial and lateral sides at the joint space against the patient's condyles. The caliper is arranged to exert a constant force against the soft tissue of the patient, for example 2 lbs. force (8.9 N), through extension and retraction. The caliper 110 is configured to align to condyle "flats" according to the patient's knee shape and size, and consistently compressing against soft tissue of the patient's leg, regardless of the soft tissue the patient may have.

The caliper 110 includes first and second jaws 112, 114 with the second jaw 114 being slidable along an elongate housing 116 extending from the first jaw 112. The jaws 112, 114 are spaced apart from one another by a predetermined, minimum distance 118, and are constantly biased toward one another by a constant force spring within the caliper. The constant force spring engages or couples to both the first and second jaws 112, 114.

A stopper 130 is formed along at least one side of the first jaw 112 that at least maintains the jaws 112, 114 in the predetermined, minimum distance, resisting the spring. The minimum distance enables easy placement of the jaws 112, 114 over the leg or knee joint so the clinician need only gently open the jaws, which lightly resists opening, as the caliper is placed over the patient's leg or knee joint.

According to this embodiment, it is preferable that the jaws 112, 114 are spaced apart to facilitate their opening and use for measuring a distance of the patient's anatomy. This starting point of the jaws, with them being spaced apart a predetermined distance and maintained in such minimum distance by the stopper 130, is indexed to a scale 140 on the housing, and eases the location and adjustment of the caliper on the patient since the predetermined distance corresponds to a minimum length of the intended dimensions for measurement.

Each of the jaws 112, 114 defines an arcuate recessed portion 120 at an inside upper end, and flat portions 121 along at least part of a middle and lower end of the jaws 112, 114. The recessed portion 120 allows for the clinician to grasp the jaws when locating the caliper over the patient's anatomy, and affords making any further adjustments to the caliper in an easy and simple manner. The recessed portion 120 is ergonomic in the sense it is contoured to receive fingers of the clinician without interfering with the flat portions 121 intended to engage and secure against the patient's anatomy.

The flat portions 121 are preferably of a sufficient width 160 that will allow the clinician to align the jaws 112, 114 to the appropriate location on the patient's anatomy. In regard to the M-L width measurement at the knee center, whether the knee is in full extension or in flexion. The flat portions are advantageous over corresponding portions in the conventional caliper since the flat portions are defined by a greater width, allowing for more even measurement and gently distribute pressure over soft tissue, and eliminate any cup-shaped profile which is found in a caliper used for knee measurement.

The flat portions provide for more flexibility in placement over the patient's anatomy as opposed to a caliper with cup-shaped profiles that are adapted for a specific location over the patient's condyle.

Each of the jaws 112, 114 defines an end point 161, 162 that has a rounded profile, as in end point 161, or a flat profile, as in end point 162. The arrangement of the end points 161, 162 has gradual form to prevent any sharp structure that may injure the patient.

The jaws 112, 114 also define contoured outer peripheries 125, 129 opposite the recessed portion 120 and flat portions 121, such that the contoured outer peripheries 125, 129 are adapted for being squeezed by the clinician. The contoured outer peripheries bow outwardly from the recessed portion and taper toward the end points 161, 162 to improve the ergonomics of the jaws when to make them more tactile when being located and adjusted by the clinician.

The caliper 110 is defined by first and second structures 111, 113, with the second structure slidably engaging the first structure, and connected to one another at least in part by the constant force spring secured within the first and second structures 111, 113. The first structure 111 defines the first jaw 112 and the housing 116, and is composed of first and second sides 122, 124 that lockingly engage one another by tabs 146 depending from the first side 122 which secure within slots 148 formed by the second side 124.

The second structure 113 defines first and second sides 126, 128 that lockingly engage one another by tabs 136 depending from the first side 126 which secure within slots 138 formed by the second side 128. This locking arrangement allows the first and second sides of the corresponding first and second structures to snap together for simple assembly and form a caliper that does not require side actions, cams, inserts, and other similar structural features frequently found in a caliper.

A pin or fastener 132 is secured in place by a nut 134 and extends across a sleeve portion 123 of the second structure 113. The sleeve portion 123 is adapted to slide along the housing 116 a variable distance from the stopper 130, with the pin 132 sliding within a slot 156 formed by the housing 116. Indicia 140 are provided along the housing 116 for measurement of the distance of the jaws. It should be remembered that the indicia are calibrated according to the predetermined distance 118.

Suitable gripping elements 166, 168 are on the first and second structures 111, 113 to facilitate adjustment of the jaws 112, 114 relative to one another. The gripping elements provide improved frictional properties for handling over the materials used to form the first and second structures. In the depicted embodiment, the gripping elements 166, 168 are at an upper side of the first and second structures, however gripping elements may be at other locations such as along the arcuate recess portions.

Figure 3:
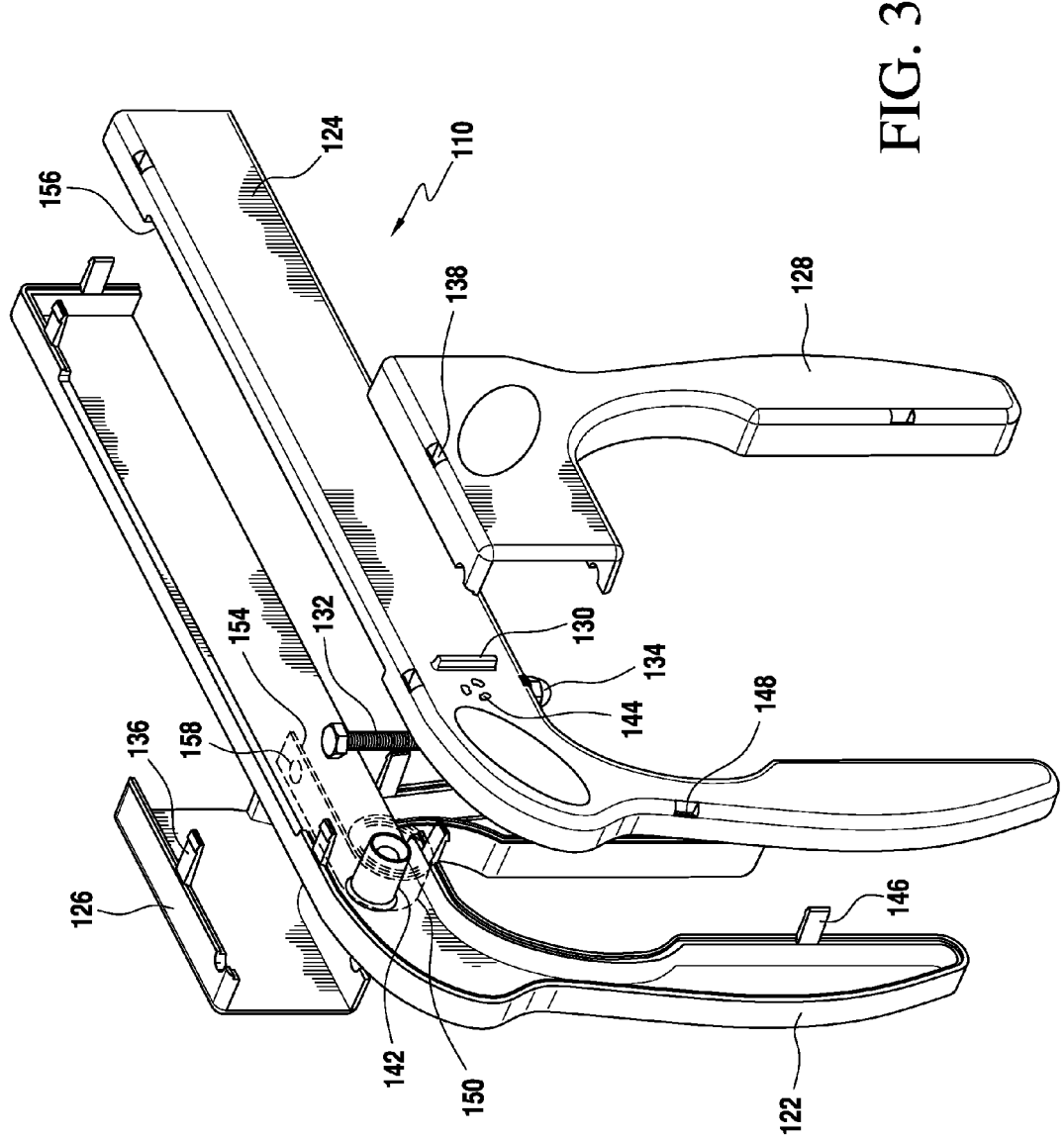
FIG. 3 is an exploded view of the caliper of FIG. 2.
Figure 4:
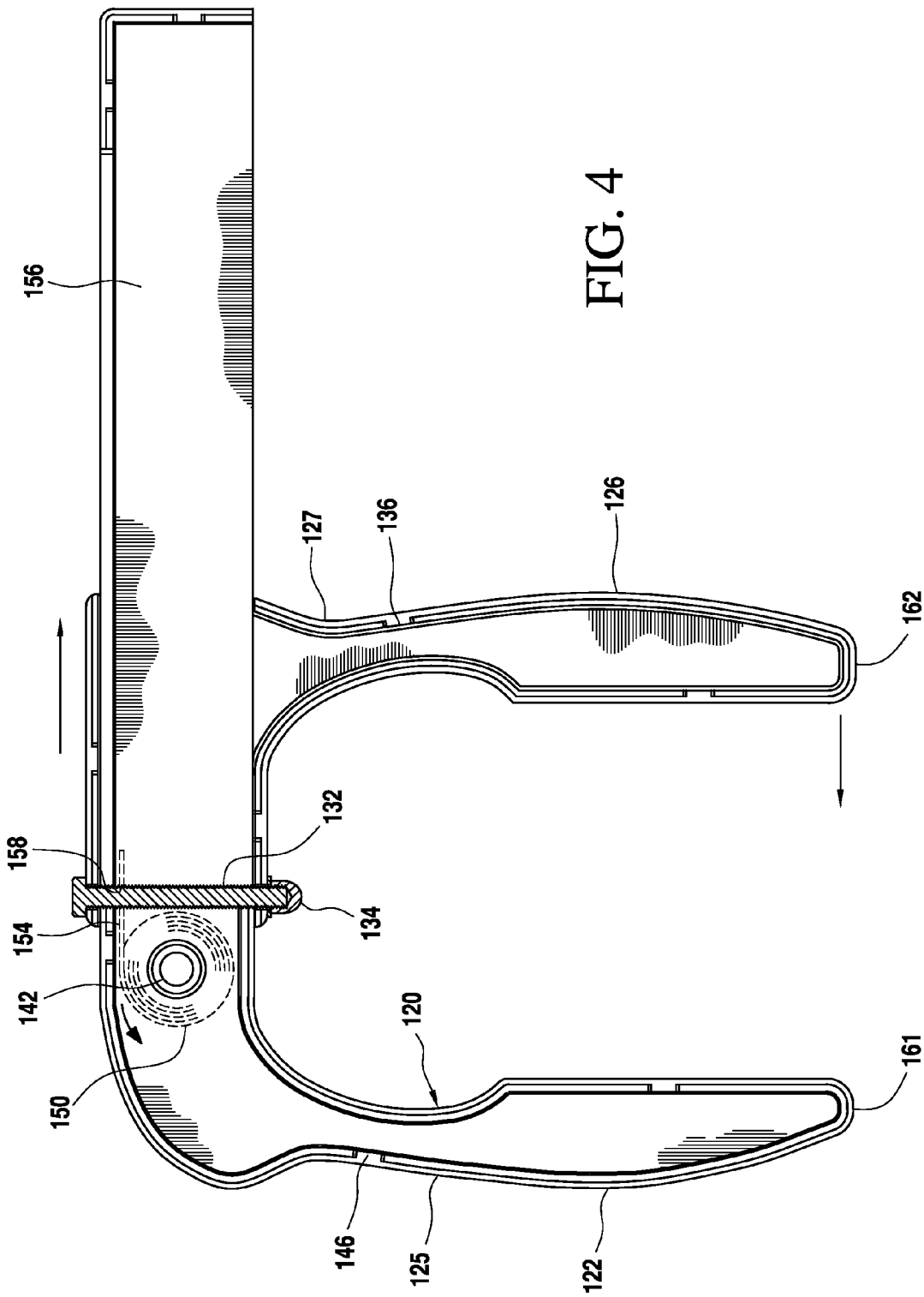
FIG. 4 is a cross-sectional view taken along line IV-IV of the caliper of FIG. 2.
Figure 5:
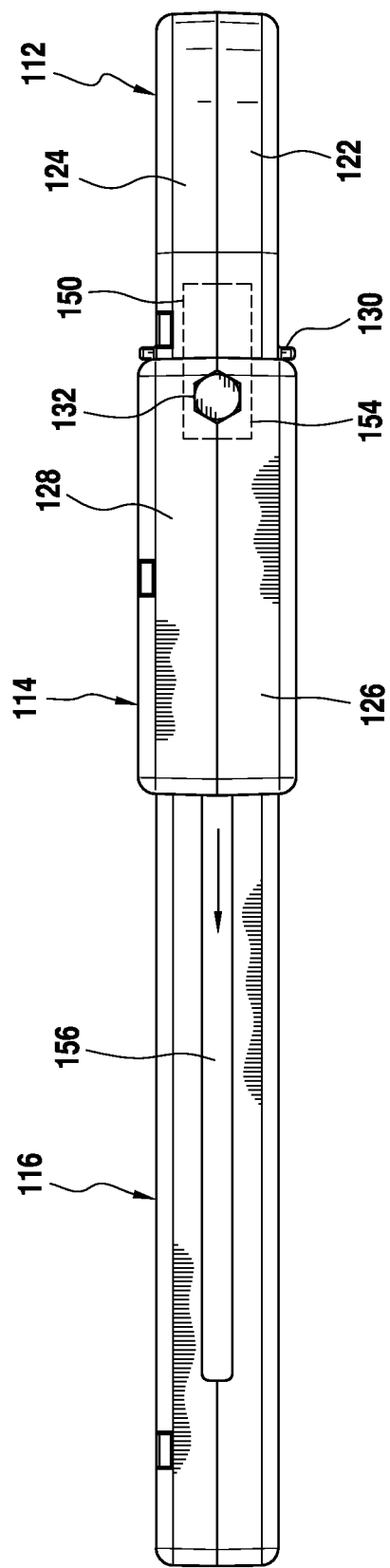
FIG. 5 is a top view of the caliper of FIG. 2.

In reference to FIGS. 3-5, the constant force spring 150 is mounted on a boss 142 extending from an interior surface of the first structure 111, and defines an end portion 154 having a hole 158 through which the pin 132 extends to couple the first and second structures 111, 113 by the spring 150. The constant force spring 150 may be constructed as a rolled ribbon of spring steel such that the spring is relaxed when it is fully rolled up. As is well-known, when the spring is unrolled, the restoring force comes primarily from the portion of the ribbon near the roll. It follows because the geometry of that region remains nearly constant as the spring unrolls, the resulting force is nearly constant.

The spring is preferably enclosed within the first and second structures 111, 113 so that when the caliper is extended and retracted, the spring cannot come into contact with the patient or clinician.

In use, the constant force spring 50 provides a constant force throughout its extension and retraction as the jaws are located and adjusted on the patient's anatomy. Preferably, the constant force spring 150 provides a constant force with at least the range of 1-3 lbs. force (7.5-10 N) to provide consistent compression of soft tissue. This provides for consistent measurement of a patient's anatomy with little soft tissue and with patients with a large amount of soft tissue. This leads to more accurate brace sizing across anatomical phenotypes.

The caliper may be employed in measuring a knee and leg under the method described in co-pending U.S. application Ser. No. 14/011,300, filed on 27 Aug., 2013.

While the caliper is explained as used to measure a patient's knee, it should be remembered that the caliper is not limited to this use, but may measure any number of a patient's anatomy and other objects for measurement.

The invention claimed is:

1. An ergonomic caliper for measuring anatomical dimensions, comprising:
    an elongate housing;
    a first jaw connected to the housing;
    a second jaw slidably connected to the housing, the first and second jaws spaced apart by a predetermined minimum distance; and
    a constant force spring engaging the first and second jaws, the constant force spring biasing the first and second jaws toward one another,
    wherein at least one of the first and second jaws defines an arcuate recessed portion configured to receive fingers at an inside upper end, and a contoured outer periphery that bows outwardly from the arcuate recessed portion and tapers toward an endpoint of the at least one of the first and second jaws, the arcuate recessed portion and the contoured outer periphery adapted for grasping with hands; and
    wherein at least one flat portion is located along at least part of a middle and lower end on an inner side of the one of the first and second jaws so as to engage a patient's anatomical structure.

2. The caliper of claim 1, further comprising a stopper located along the first jaw and arranged to maintain the first and second jaws apart by a predetermined minimum distance.

3. The caliper of claim 1, wherein the predetermined minimum distance is indexed to a scale on the housing.

4. The caliper of claim 1, wherein at least one of the first and second jaws defines an end point having a generally rounded profile.

5. The caliper of claim 1, wherein the constant force spring is mounted on a boss extending from an internal surface of the housing located proximate to the first jaw, the constant force spring having an end portion connected to the second jaw.

6. The caliper of claim 5, wherein the constant force spring is rotatably mounted about the boss and permitting extension of the end portion relative to the boss.

7. The caliper of claim 5, further comprising a pin extending through the end portion of the constant force spring and extending through the second jaw.

8. The caliper of claim 7, wherein the housing defines an elongate slot extending generally proximate from the boss toward an end portion remote from the first jaw.

9. The caliper of claim 8, wherein the second jaw is arranged to slide relative to the slot and generally along the length of the slot.

10. The caliper of claim 1, wherein the first jaw and housing form a generally continuous structure formed by opposed sides joining one another.

11. The caliper of claim 1, wherein the second jaw defines opposed parts slidably mounted over the housing.

12. A method for measuring a knee for a knee brace using the caliper of claim 1, comprising the steps of:
    placing both hands on the caliper with one hand grasping around the arcuate recessed portion and the contoured outer periphery of the first jaw and one hand grasping around the arcuate recessed portion and the contoured outer periphery of the second jaw;
    placing the caliper proximate to a portion of the knee;
    pulling the second jaw against a force exerted by the constant force spring wider than a width of the knee;
    placing the flat portion of the first jaw on a first outer condyle of the knee;
    releasing the second jaw to place the flat portion of the second jaw on a second outer condyle of the knee opposite the first outer condyle;
    adjusting the first and second jaws with the hands to align the flat portions of the first and second jaw on the outer condyles; and
    with the caliper placed around the knee, reading a measurement of a distance defined by the flat portions of the first and second jaws against indicia along the housing of the caliper.

13. The method of claim 12, further comprising the step of pulling the second jaw away from the knee or leg under force exerted by the constant force spring.

14. The method of claim 13, further comprising the steps of pulling the caliper away from the knee or leg, and releasing the second jaw so as to place the first and second jaws apart from one another at said predetermined distance.

15. The caliper of claim 1, further comprising at least one generally oblong gripping element located at an upper end of one of the first and second jaws and configured for placement of at least a portion of one hand in forming a frictional grip.

16. A caliper for measuring an anatomical circumference, comprising:
    an elongate housing;
    a first jaw connected to the housing;
    a second jaw slidably connected to the housing and along a slot defined by the housing, the first and second jaws spaced apart by a predetermined minimum distance;
    a constant force spring engaging the first and second jaws, the constant force spring biasing the first and second jaws toward one another by a force of 1 lb. to 3 lbs.;
    a pin connecting a first end of the constant force spring to the second jaw and extending at least in part through the slot, the pin arranged and configured for sliding within the slot; and
    wherein the first and second jaws are each defined by first and second structures that lockingly engage one another by tabs on first sides which secure within slots on second sides, the securement of the first and second structures of the first jaw forming the slidable housing around the second jaw.

17. The caliper of claim 16, wherein the constant force spring is a rolled ribbon of spring steel such that the spring is relaxed when it is at least substantially fully rolled.

* * * * *